(12) United States Patent
Porter et al.

(10) Patent No.: US 11,561,231 B2
(45) Date of Patent: Jan. 24, 2023

(54) THROMBOGENICITY TEST APPARATUS AND ASSOCIATED METHODS

(71) Applicant: St. Jude Medical, Cardiology Division, Inc., St. Paul, MN (US)

(72) Inventors: Deanna Porter, Cottage Grove, MN (US); Kent Grove, Sartell, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 754 days.

(21) Appl. No.: 16/375,413

(22) Filed: Apr. 4, 2019

(65) Prior Publication Data

US 2019/0323059 A1 Oct. 24, 2019

Related U.S. Application Data

(60) Provisional application No. 62/685,023, filed on Jun. 14, 2018, provisional application No. 62/661,948, filed on Apr. 24, 2018.

(51) Int. Cl.
| | |
|---|---|
| *G01N 33/86* | (2006.01) |
| *A61L 33/00* | (2006.01) |
| *C12Q 1/56* | (2006.01) |
| *G01M 99/00* | (2011.01) |

(52) U.S. Cl.
CPC .......... *G01N 33/86* (2013.01); *A61L 33/0005* (2013.01); *A61L 33/0011* (2013.01); *C12Q 1/56* (2013.01); *G01M 99/002* (2013.01); *A61L 2300/42* (2013.01)

(58) Field of Classification Search
CPC .. A61L 33/0005; A61L 2300/42; G01N 33/86
See application file for complete search history.

(56) References Cited

U.S. PATENT DOCUMENTS

| | | | | |
|---|---|---|---|---|
| 2010/0139375 A1* | 6/2010 | Johns | ..................... | G01N 11/08 |
| | | | | 73/54.24 |
| 2015/0096225 A1* | 4/2015 | Gervais | ................... | A01G 9/24 |
| | | | | 47/17 |

OTHER PUBLICATIONS

Cunningham, Matthew et al. "Thrombogenicity Testing for BloodContacting Medical Devices in an in vitro Ovine Blood Loop: Design Improvements and Continuing Validation" Proceedings of the 2017 Design of Medical Devices Conference, Apr. 10-13, 2017. (Year: 2017).*

(Continued)

*Primary Examiner* — Paul M. West
(74) *Attorney, Agent, or Firm* — Wiley Rein LLP

(57) ABSTRACT

An apparatus for in vitro testing of medical device thrombogenicity includes an enclosure; a heating element thermally coupled to the enclosure; and a temperature feedback circuit operably coupled to the heating element and configured to control the heating element to maintain an interior of the enclosure within a preset temperature range. Positive, negative, and intermediate control rods are provided as standards against which to compare a medical device test article. Multiple blood test loops can be established through the enclosure using a common blood supply. The medical device test article can be placed in one of the loops, while the remaining loops can contain controls. Blood can be circulated through the test loops at a flow rate similar to that encountered in vivo, and thrombus formation can be assessed thereafter.

18 Claims, 11 Drawing Sheets

(56) References Cited

OTHER PUBLICATIONS

Grove et al., Thrombogenicity Testing of Medical Devices in a Minimally Heparinized Ovine Blood-Loop, Journal of Medical Devices, 2017.

* cited by examiner

THROMBOGENICITY TEST APPARATUS AND ASSOCIATED METHODS

CROSS-REFERENCE TO RELATED APPLICATIONS

This application claims the benefit of U.S. provisional application Nos. 62/661,948, filed 24 Apr. 2018 ("the '948 application") and 62/685,023, filed 14 Jun. 2018 ("the '023 application"). The '948 and '023 applications are hereby incorporated by reference as though fully set forth herein.

BACKGROUND

The present disclosure relates generally to medical devices. In particular, the present disclosure relates to apparatuses, systems, and methods for testing medical device thrombogenicity.

Medical devices for use in contact with circulating blood must be assessed for thrombogenicity in accordance with ISO 10993-4. Extant methodologies for testing thrombogenicity utilize an in vivo procedure in a canine model. Such methodologies are associated with various challenges, including anatomy, animal variability, limited data sets, and a lack of controls for comparison. Such methodologies also disadvantageously require that the test animals be euthanized following the thrombogenicity studies.

Grove et al., "Thrombogenicity Testing of Medical Devices in a Minimally Heparinized Ovine Blood-Loop," published in 2017 in the Journal of Medical Devices, discloses an in vitro method for testing medical device thrombogenicity.

BRIEF SUMMARY

Disclosed herein is an apparatus for testing thrombogenicity of a medical device, the apparatus comprising: an enclosure; a heating element thermally coupled to the enclosure; and a temperature feedback circuit operably coupled to the heating element and configured to control the heating element to maintain an interior of the enclosure within a preset temperature range. The apparatus also includes positive and negative thrombogenicity control rods, and optionally an intermediate control rod, each of which includes a saddle portion, a base portion, and a neck portion connecting the saddle portion and the base portion.

Various patterns are contemplated for the positive control rods. For instance, the base portion of the positive control rod can include a helical pattern, a boss pattern, and/or a protrusion pattern.

According to aspects of the disclosure, the neck portion of a respective control rod forms an angle of about 155 degrees with the base portion of the respective control rod, in order to minimize turbulence about the control rod. Similarly, a transition between the neck portion of a respective control rod and the base portion of the respective control rod can have a radius of curvature of 0.46 inches, again to minimize turbulence about the control rod.

The apparatus can also include a plurality of thrombogenicity test loops, each thrombogenicity test loop including: a peristaltic pump; and a tubing loop, wherein a first portion of the tubing loop is positioned within the peristaltic pump and a second portion of the tubing loop is positioned within the enclosure. At least one tubing loop can include an expanded diameter region, positioned within the enclosure, in order to accommodate a high-profile (e.g., large diameter) medical device test article.

The temperature feedback circuit can include a thermostat controller.

Also disclosed herein are control rods for use in testing thrombogenicity of a medical device. Each control rod includes: a saddle portion; a base portion; and a neck portion connecting the saddle portion and the body portion. The base portion of the control rod is configured to cause a desired thrombogenic response when exposed to blood flow.

For instance, the base portion of the control rod can be configured to cause a positive thrombogenic response when exposed to blood flow. In embodiments of the disclosure, therefore, the base portion of the control rod can include a helical pattern, a boss pattern, and/or a protrusion pattern.

The instant disclosure also provides a method of testing thrombogenicity of a medical device. The method includes establishing a testing apparatus including: an enclosure; a heating element thermally coupled to the enclosure; and a temperature feedback circuit operably coupled to the heating element and configured to control the heating element to maintain an interior of the enclosure within a preset temperature range. The method also includes establishing a plurality of thrombogenicity test loops, at least a portion of each of the plurality of thrombogenicity test loops being disposed within the enclosure of the testing apparatus; inserting, into respective ones of the plurality of thrombogenicity test loops, a positive thrombogenicity control rod, a negative thrombogenicity control rod, and a medical device test article; circulating blood through the plurality of thrombogenicity test loops; and evaluating thrombogenicity of the medical device test article by comparison to the positive thrombogenicity control rod and the negative thrombogenicity control rod.

The preset temperature range can be about 37±2 degrees Celsius.

The positive thrombogenicity control rod can include a helical pattern, a boss pattern, and or a protrusion pattern.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides apparatuses, systems, and methods for testing the thrombogenicity of a medical device in vitro. Advantageously, the apparatuses, systems, and methods disclosed herein address many of the challenges present in extant, in vivo, thrombogenicity tests. For instance, in vitro testing increases control over the thrombogenicity evaluation by reducing animal and test apparatus variability. First, all articles under testing (e.g., the medical device being tested and any controls) can be tested using blood from the same donor animal to assess changes over the course of a medical device design development cycle. Second, the apparatuses disclosed herein include consistent, uniform controls, designed to produce specific thrombogenic responses when exposed to blood, against which the thrombogenic response of a medical device being tested can be compared. In vitro testing according to aspects of the disclosure eliminates the need to euthanize animals post-testing, as the required blood volume is reduced below the threshold at which euthanasia is mandatory. In addition, in vitro testing can be used to evaluate coatings utilized on medical device materials as well as to optimize device-specific anticoagulation regimens to simulate clinical intended use for a medical device.

Figure 1:
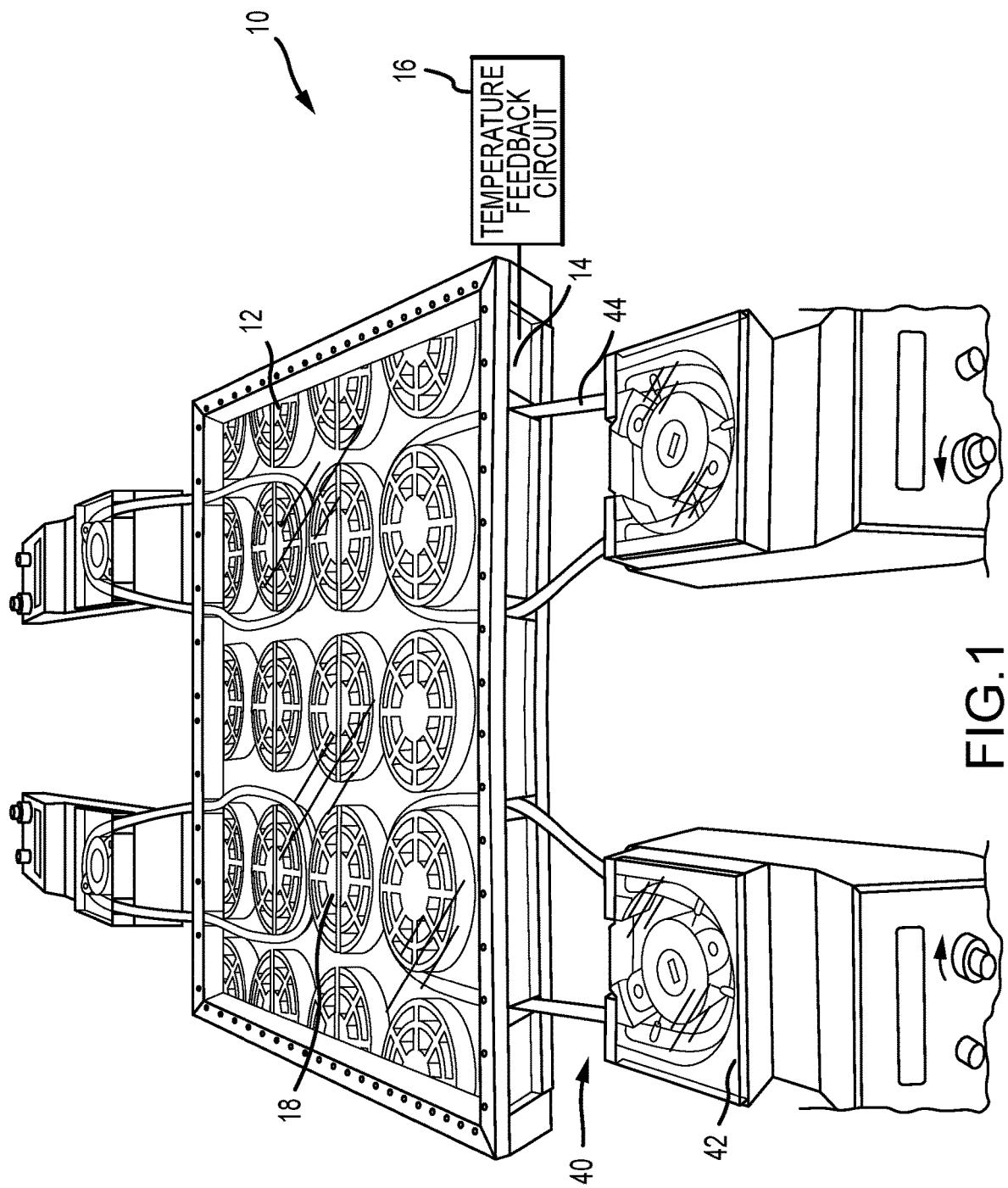
FIG. 1 depicts an apparatus for testing thrombogenicity of a medical device.

FIG. 1 depicts a test apparatus (also referred to herein as a "heating table") 10 for testing the thrombogenicity of a medical device. Heating table 10 generally includes an enclosure 12, a heating element 14 thermally coupled to enclosure 12, and a temperature feedback circuit 16 (shown schematically), including a thermostat controller, operably coupled to heating element 14.

According to aspects of the disclosure, enclosure 12 is an acrylic case with stainless steel bracing. Although the overall size of enclosure 12 can vary, in general it should be large enough to accommodate a plurality of blood test loops as disclosed herein. Enclosure 12 can also incorporate a grid system 18, such as the model FH-102 EasyFloor® grid module for radiant floor heating from FloorHeat Company, to help guide the blood test loops through the interior of enclosure 12. It should be understood, however, that the construction of enclosure 12 can vary from the foregoing description without departing from the scope of the instant disclosure.

Heating element 14 radiates heat into the interior of enclosure 12 to maintain the interior of enclosure 12 within a preset temperature range (e.g., about 37±2 degrees Celsius) for thrombogenicity testing. In aspects of the disclosure, heating element 14 incorporates heating tape, such as those commercially available from BriskHeat® Corporation of Columbus, Ohio. Heating element 14 can also incorporate a radiator, such as an aircraft aluminum enclosure, to improve heat transfer into the interior of enclosure 12.

FIGS. 2A-2C and 3A-3C depict various thrombogenicity control rods for use in connection with the instant disclosure. Thrombogenicity control rods disclosed herein can be classified as positive, negative, or intermediate. As used herein, the term "positive control rod" refers to a control rod that is designed to be thrombolytic (e.g., thrombus covering about 51% or more of the control rod surface), the term "negative control rod" refers to a control rod that is designed not to be thrombolytic (e.g., thrombus covering less than about 25% of the control rod surface), and the term "intermediate control rod" refers to a control rod that is designed to be partially thrombolytic (e.g., thrombus covering between about 25% and about 51% of the control rod surface).

Figure 2A:
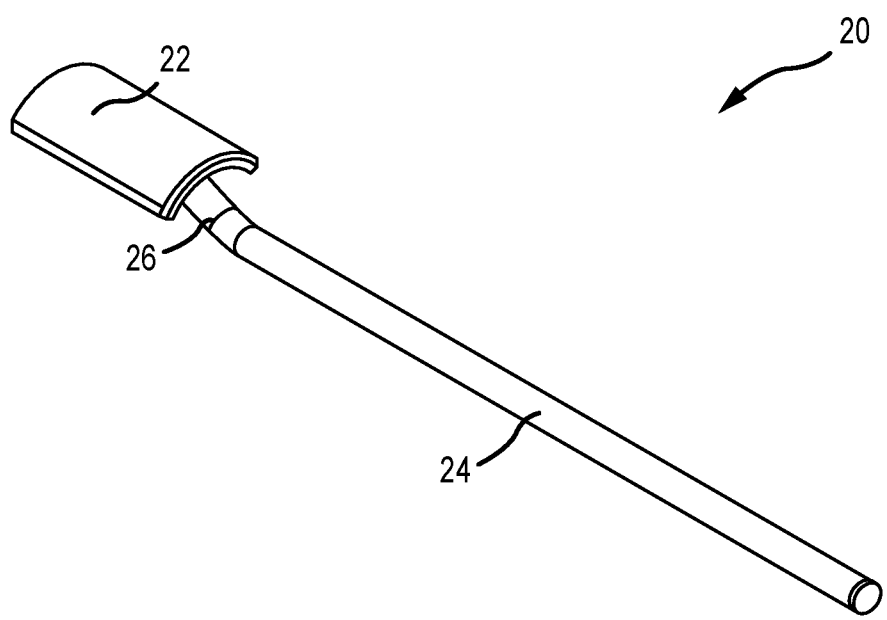
FIG. 2A is a perspective view of a negative control rod according to aspects of the instant disclosure.
Figure 2B:
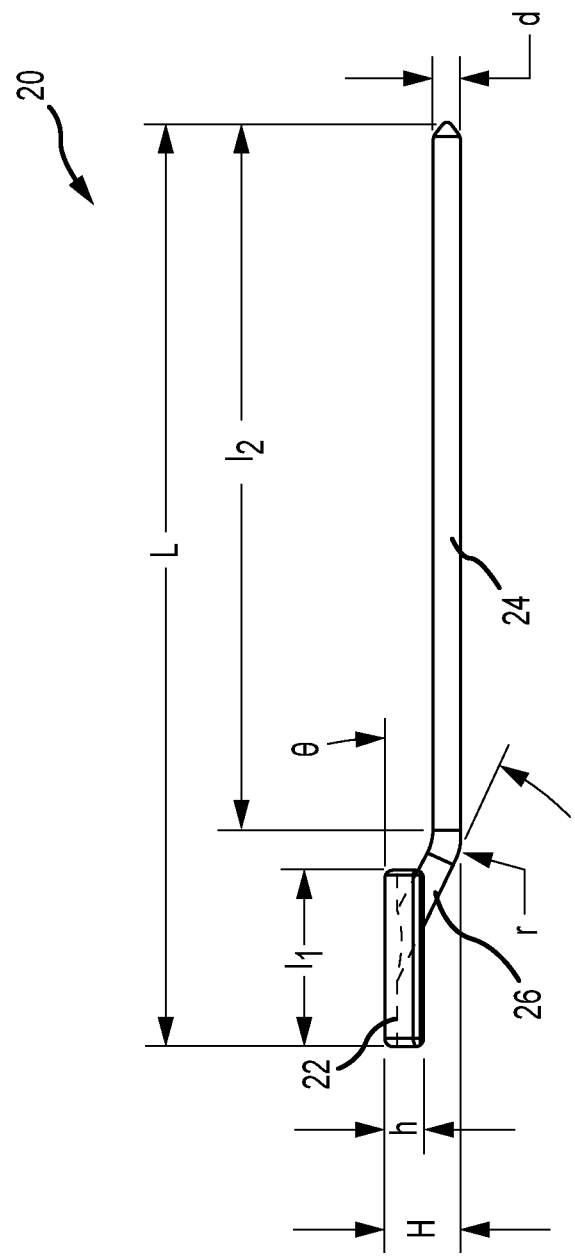
FIG. 2B is a front view of the negative control rod of FIG. 2A.

Certain features common to multiple control rods disclosed herein will be discussed with reference to the illustrative negative control rod 20 depicted in FIGS. 2A-2C. It should be understood, however, that the dimensions disclosed herein are merely exemplary and can vary from embodiment to embodiment without departing from the scope of the instant disclosure.

Negative control rod 20 includes a saddle portion 22, a base portion 24, and a neck portion 26. Referring to FIG. 2B, the overall length L of control rod 20 can be between about 3 inches and about 7 inches; in one embodiment, the overall length L of control rod 20 is about 5.23 inches. The overall height H of control rod 20 can be between about 0.2 inches and about 0.6 inches; in one embodiment, the overall height H of control rod 20 is about 0.43 inches.

Figure 2C:
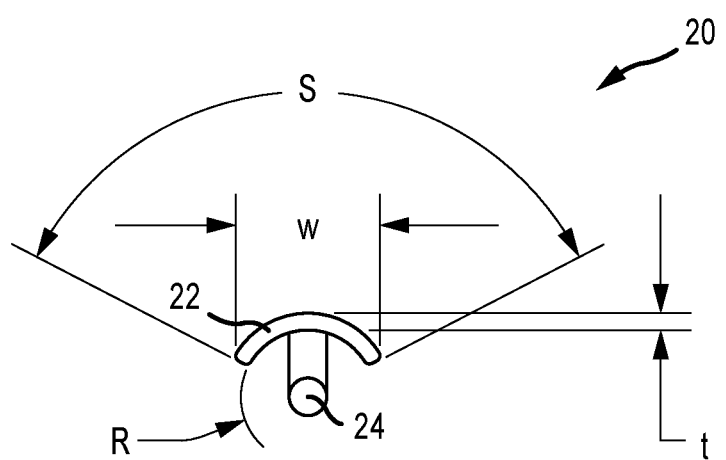
FIG. 2C is a right-side view of the negative control rod of FIG. 2A.

Referring to FIG. 2C, saddle portion 22 is arcuate and can have an arc length S of about 125.3 degrees and a radius of curvature R of about 0.28 inches (though other dimensions are contemplated). As shown in FIGS. 2B and 2C, embodiments of saddle portion 22 have a length $l_1$ of between about 0.5 inches and about 2 inches; in one embodiment, the length $l_1$ of saddle portion 20 is about 1 inch. Likewise, embodiments of saddle portion 22 have a width w of between about 0.3 inches and about 0.8 inches; in one embodiment, the width w of saddle portion 22 is about 0.59 inches. Embodiments of saddle portion 22 have a height h of about 0.22 inches and a thickness t of about 0.07 inches, though other heights and thicknesses are within the scope of the instant disclosure. In use, as discussed in greater detail below, saddle portion 22 sits on the exterior of a test loop (e.g., on the outside surface of a length of tubing) to position control rod 20 within the test loop.

Base portion 24, which fits within a test loop (e.g., within the interior of a length of tubing) can have a diameter d of between about 0.16 inches and about 0.4 inches and a length $l_2$ between about 3 inches and about 7 inches. In one embodiment, the diameter d of base portion 24 is about 0.16 inches and the length $l_2$ of base portion 24 is about 4.01 inches.

Neck portion 26 connects saddle portion 22 to base portion 24. In embodiments of the disclosure, neck portion 26 forms an angle Θ of between about 15 degrees and about 35 degrees, and in one embodiment of the disclosure of about 25 degrees (and thus forms an angle of about 155 degrees with base portion 24), with saddle portion 22, which desirably minimizes turbulence of blood flow about control rod 20 when in use. The radius of curvature r at the joint between neck portion 26 and base portion 24 can be about 0.46 inches.

Negative control rod 20 can be formed using additive manufacturing techniques, such as 3-D printing, via injection molding, or via any other suitable manufacturing technique. In some embodiments, negative control rod 20 is formed of a hydroxylated wax material, such as VisiJet® S100 support material from 3D Systems, Inc.

Figure 3A:
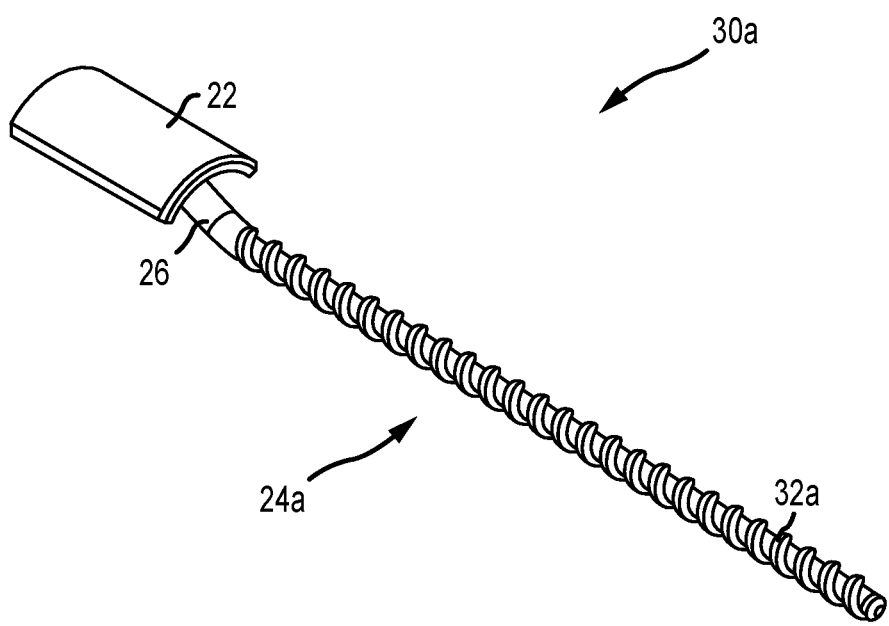
FIGS. 3A through 3C depict, in perspective view, various embodiments of positive control rods according to aspects of the instant disclosure.
Figure 3B:
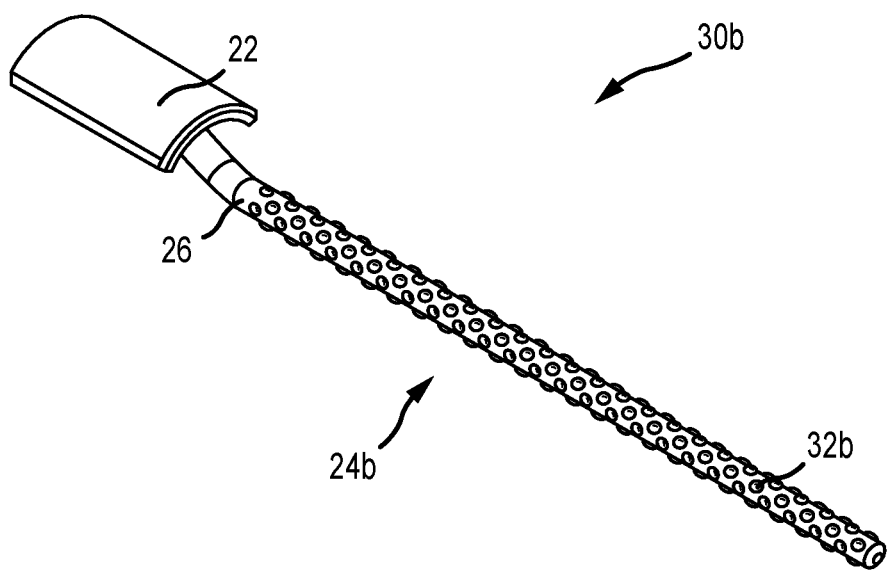
Figure 3C:
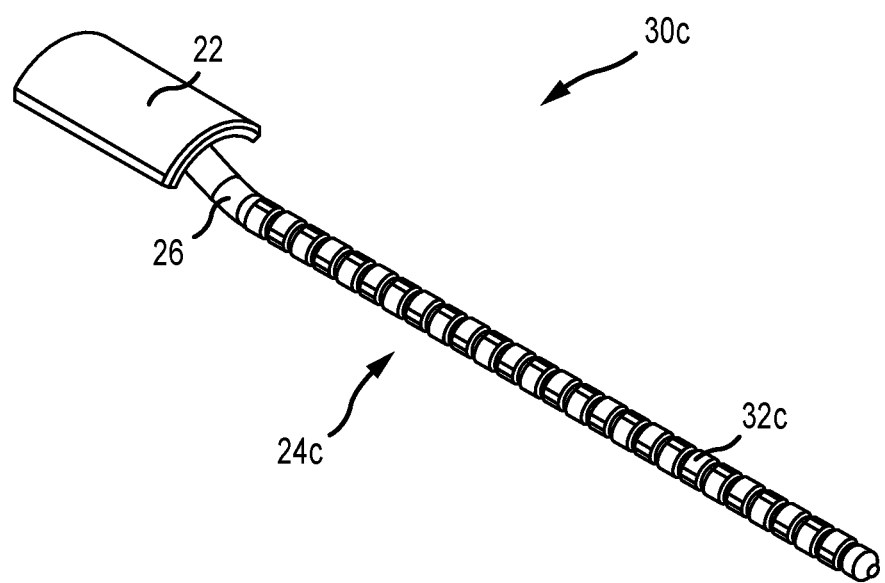

FIGS. 3A-3C depict various positive control rods 30 (e.g., 30a, 30b, and 30c). The dimensions of positive control rods 30a, 30b, 30c are generally similar to those discussed above with reference to negative control rod 20. Positive control rods 30a, 30b, 30c, however, include thrombogenic features on their respective base portions 24a, 24b, 24c.

For instance, as shown in FIG. 3A, base portion 24a of positive control rod 30a includes a helical pattern 32a. In embodiments of the disclosure, helical pattern 32a has a thread width of between about 0.05 inches and about 0.2 inches and a pitch of about 0.160 inches.

As another example, as shown in FIG. 3B, base portion 24b of positive control rod 30b includes a plurality of bosses 32b arranged in circumferential rows. Each circumferential row can include four bosses 32b, spaced equally about the circumference of base portion 24b (e.g., at about 90 degree intervals), with adjacent rows offset from each other by about half the interval between bosses 32b (e.g., about 45 degrees offset). The rows of bosses 32b can be spaced apart from each other along the length of base portion 24b by about 0.081 inches. Each individual boss 32b can have a diameter of between about 0.02 inches and about 0.2 inches; in one embodiment, each boss 32b has a diameter of about 0.05 inches. Each boss 32b can have a height above base portion 24b of between about 0.02 inches and about 0.2 inches.

Still another exemplary positive control rod 30c is shown in FIG. 3C. Positive control rod 30c includes a plurality of protrusions 32c on its base portion 24c.

Positive control rods 30a, 30b, 30c can be formed using additive manufacturing techniques, such as 3-D printing, via injection molding, or via any other suitable manufacturing technique. In some embodiments, positive control rods 30a, 30b, 30c are formed of acrylonitrile butadiene styrene ("ABS") or VeroClear, a transparent material commercially available from Stratasys Ltd that simulates polymethyl methacrylate ("PMMA").

Those of ordinary skill in the art will appreciate from the instant disclosure that the thrombogenic response of a given control rod can be manipulated by altering the patterns on base portions 24a, 24b, 24c, allowing a positive control rod (e.g., 30a, 30b, 30c) to be modified into an intermediate control rod (as defined above). For instance, helical pattern 32a, bosses 32b, or protrusions 32c can be limited to only a section of the length of base portions 24a, 24b, 24c, respectively (e.g., the first or last quarter of the overall length). As another example, the pitch of helical pattern 32a can be increased, or the density of bosses 32b or protrusions 32c along the length of base portions 24b, 24c can be reduced.

FIG. 1 also depicts a plurality of thrombogenicity test loops 40. Each test loop 40 includes a peristaltic pump 42 and a tubing loop 44, a portion of which is positioned within enclosure 12 (and thus maintained within the preset temperature range discussed above when in use).

Each tubing loop 44 has a total volume of about 100 mL. Thus, in a four-loop test as described herein, the total volume of blood required is about 400 mL. This is desirable because it minimizes, and can indeed eliminate, the need to euthanize the blood donor animal.

Figure 4:
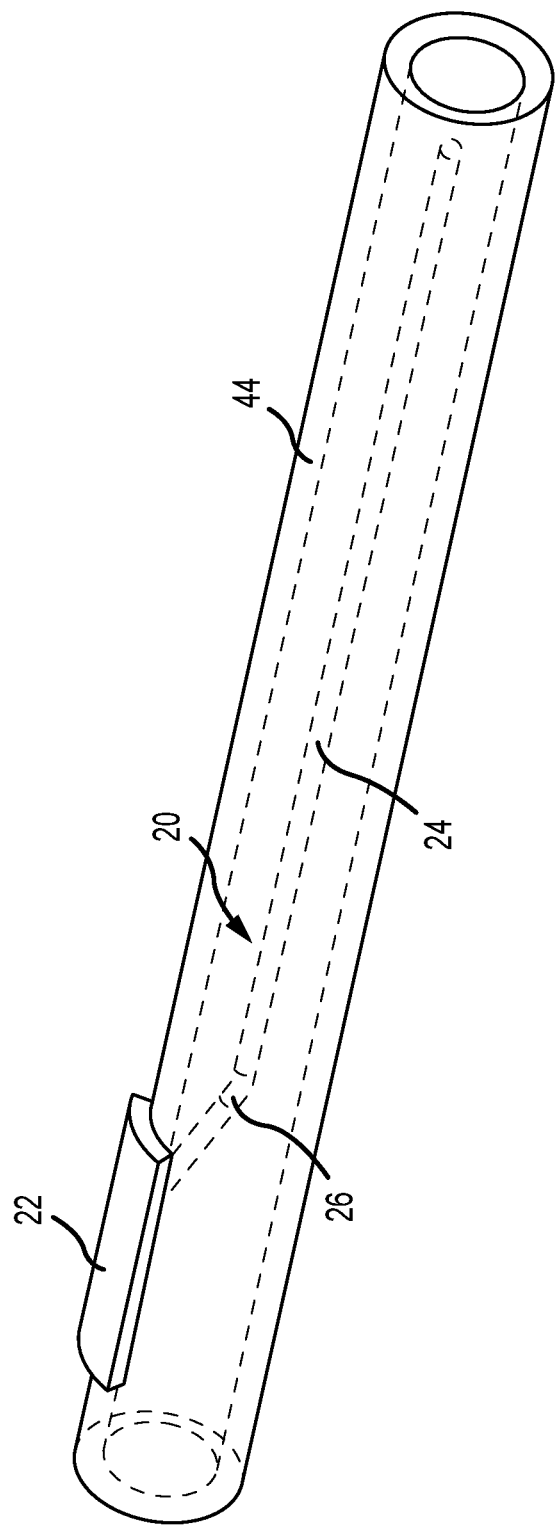
FIG. 4 illustrates use of a control rod, such as depicted in FIG. 2.

In use, one test loop 40 is a positive control loop (e.g., it contains positive control rod 30a, 30b, or 30c); one test loop 40 is a negative control loop (e.g., it contains negative control rod 20); and one test loop 40 contains a medical device test article (e.g., a medical device as to which thrombogenicity is to be evaluated). A fourth test loop 40 can contain an approved reference medical device or an intermediate control rod. For purposes of illustration, FIG. 4 shows a control rod 20 inserted within a tubing loop 44.

Fresh or stored blood is added to each tubing loop 44 and circulated therethrough using peristaltic pumps 42, while temperature feedback circuit 16 controls heating element 14 to maintain the temperature of the circulating blood within the preset range (e.g., about 37±2 degrees Celsius). In embodiments of the disclosure, the flow rate of blood through each tubing loop 44 is between about 0.5 L/min and about 0.8 L/min, which is an intermediate flow rate between typical arterial and venous flow rates. Of course, the flow rate can be varied without departing from the scope of the disclosure. For instance, the flow rate can be tailored to the intended use of the medical device test article (e.g., increased for test articles intended for arterial use and decreased for test articles intended for venous use).

After circulating blood through the test loops 40 for a sufficient amount of time (e.g., about 4 hours), the control rods and medical device test article can be removed from their respective tubing loops 44. The thrombogenicity of the medical device test article can be determined by comparing thrombus formation thereon to thrombus formation on the control rods.

Those of ordinary skill in the art will appreciate that the medical device test article should not contact the wall of its respective tubing loop 44. Thus, to accommodate larger diameter medical device test articles, such as electrophysiology mapping catheters, heart valves, sensor-enabled complex catheter systems, embolic protection systems, and the like, a portion of tubing loop 44 can have an expanded diameter. The length of tubing loop 44 can be reduced accordingly in order to maintain the total volume of tubing loop 44 substantially constant at about 100 mL.

Figure 5A:
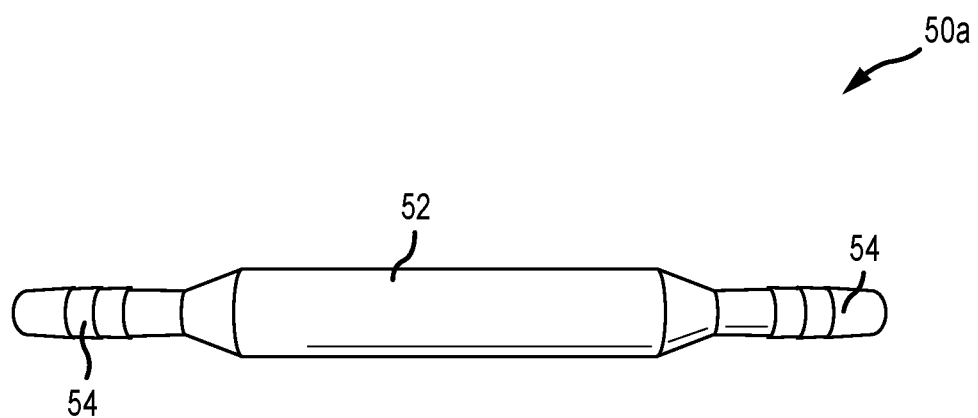
FIGS. 5A through 5C depict various embodiments of a chamber for use with medical device test articles having large diameters.
Figure 5B:
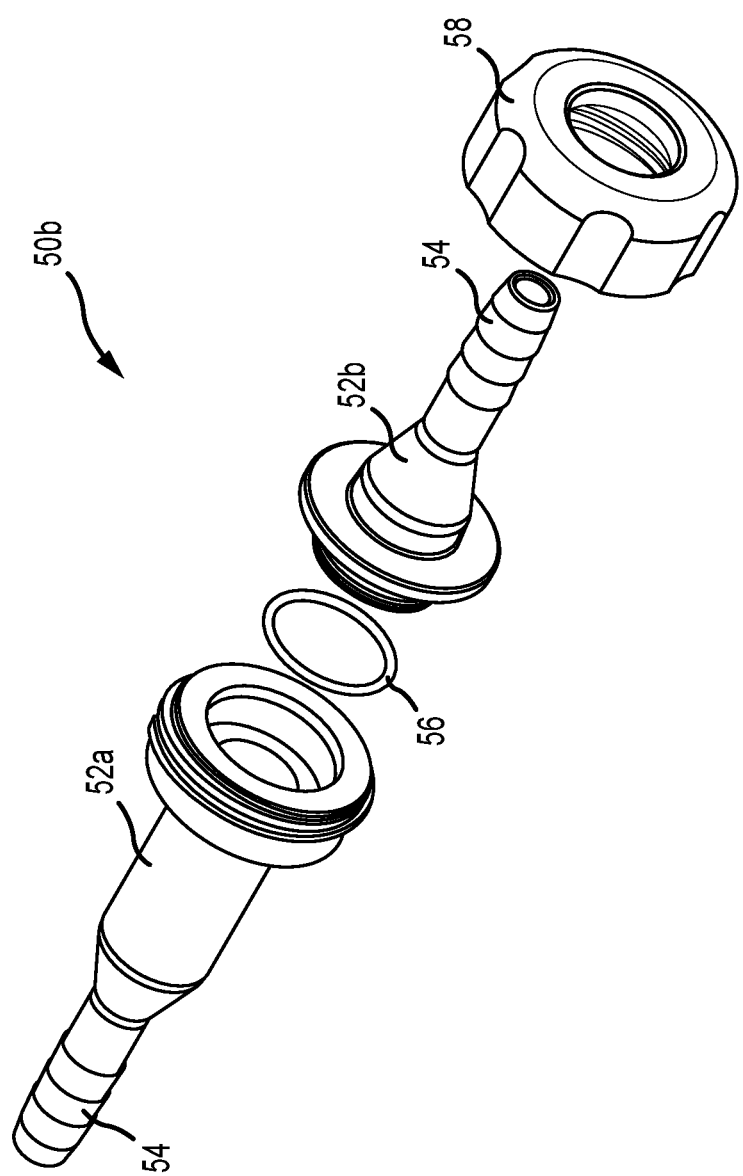
Figure 5C:
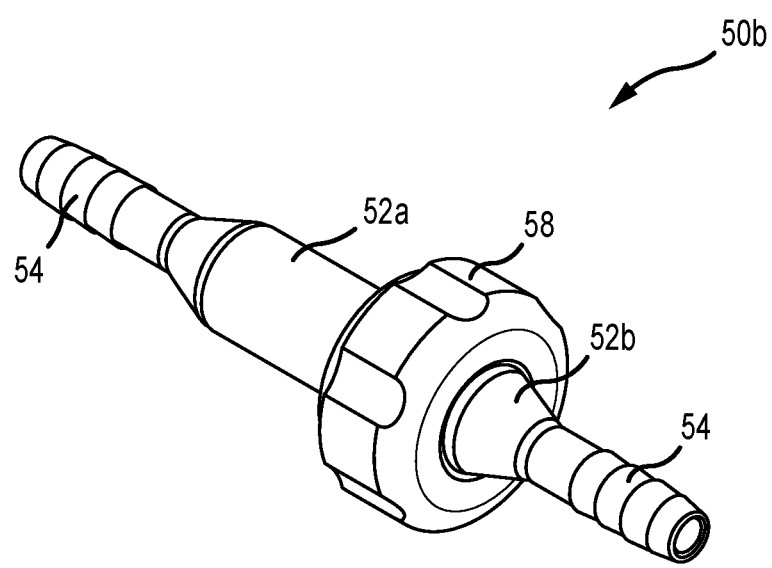

FIGS. 5A-5C depict embodiments of an expanded diameter region of tubing loop 44, referred to herein as a chamber 50. Chamber 50a, shown in FIG. 5A, is an integrated component that includes an expanded diameter central region 52 between two smaller diameter ends 54.

FIGS. 5B and 5C depict a multi-component chamber 50b in exploded and assembled views, respectively. When assembled, multi-component chamber 50b also includes an expanded diameter central region 52 between two smaller diameter ends 54, but the expanded diameter central region 52 is formed by two segments 52a and 52b on two distinct components. An O-ring 56 seals the junction between segments 52a and 52b, while a locking cap 58 secures segments 52a and 52b together.

In general, chamber 50, whether integral (e.g., chamber 50a) or multi-component (e.g., chamber 50b) can be formed via using additive manufacturing techniques, such as 3-D printing, via injection molding, or via any other suitable manufacturing technique. Suitable materials for chamber 50 include, without limitation, the materials described above in connection with negative control rod 20 and positive control rods 30.

Although several embodiments have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus for testing thrombogenicity of a medical device, the apparatus comprising:
   an enclosure;
   a heating element thermally coupled to the enclosure;
   a temperature feedback circuit operably coupled to the heating element and configured to control the heating element to maintain an interior of the enclosure within a preset temperature range; and a plurality of thrombogenicity control rods, each thrombogenicity control rod including a saddle portion, a base portion, and a neck portion connecting the saddle portion and the base portion, and wherein the plurality of thrombogenicity control rods comprises a positive control rod and a negative control rod.

2. The apparatus according to claim 1, wherein the plurality of thrombogenicity control rods further comprises an intermediate control rod.

3. The apparatus according to claim 1, wherein the base portion of the positive control rod comprises a helical pattern.

4. The apparatus according to claim 1, wherein the base portion of the positive control rod comprises a boss pattern.

5. The apparatus according to claim 1, wherein the base portion of the positive control rod comprises a protrusion pattern.

6. The apparatus according to claim 1, wherein the neck portion of a respective control rod forms an angle of 155 degrees with the base portion of the respective control rod.

7. The apparatus according to claim 1, wherein a transition between the neck portion of a respective control rod and the base portion of the respective control rod has a radius of curvature of 0.46 inches.

8. The apparatus according to claim 1, further comprising a plurality of thrombogenicity test loops, each thrombogenicity test loop comprising:
   a peristaltic pump; and
   a tubing loop, wherein a first portion of the tubing loop is positioned within the peristaltic pump and a second portion of the tubing loop is positioned within the enclosure.

9. The apparatus according to claim 8, wherein the tubing loop of at least one of the plurality of thrombogenicity test loops comprises an expanded diameter region positioned within the enclosure.

10. The apparatus according to claim 1, wherein the temperature feedback circuit comprises a thermostat controller.

11. A method of testing thrombogenicity of a medical device, the method comprising:
   establishing a testing apparatus comprising:
      an enclosure;
      a heating element thermally coupled to the enclosure; and
      a temperature feedback circuit operably coupled to the heating element and configured to control the heating element to maintain an interior of the enclosure within a preset temperature range;
   establishing a plurality of thrombogenicity test loops, at least a portion of each of the plurality of thrombogenicity test loops being disposed within the enclosure of the testing apparatus;
   inserting, into respective ones of the plurality of thrombogenicity test loops, a plurality of thrombogenicity control rods comprising:
      a positive thrombogenicity control rod;
      a negative thrombogenicity control rod; and
      a medical device test article;
   wherein each thrombogenicity control rod of the plurality of thrombogenicity control rods includes a saddle portion, a base portion, and a neck portion connecting the saddle portion and the base portion;
   circulating blood through the plurality of thrombogenicity test loops; and
   evaluating thrombogenicity of the medical device test article by comparison to the positive thrombogenicity control rod and the negative thrombogenicity control rod.

12. The method according to claim 11, wherein the preset temperature range comprises 37±2 degrees Celsius.

13. The method according to claim 11, wherein the positive thrombogenicity control rod comprises a helical pattern.

14. The method according to claim 11, wherein the positive thrombogenicity control rod comprises a boss pattern.

15. The method according to claim 11, wherein the positive thrombogenicity control rod comprises a protrusion pattern.

16. A control rod for use in testing thrombogenicity of a medical device, the control rod comprising:
   a saddle portion;
   a base portion; and
   a neck portion connecting the saddle portion and the body portion,
   wherein the base portion of the control rod comprises a helical pattern configured to cause a positive thrombogenic response when exposed to blood flow.

17. A control rod for use in testing thrombogenicity of a medical device, the control rod comprising:
   a saddle portion;
   a base portion; and
   a neck portion connecting the saddle portion and the body portion,
   wherein the base portion of the control rod comprises a boss pattern configured to cause a positive thrombogenic response when exposed to blood flow.

18. A control rod for use in testing thrombogenicity of a medical device, the control rod comprising:
   a saddle portion;
   a base portion; and
   a neck portion connecting the saddle portion and the body portion,
   wherein the base portion of the control rod comprises a protrusion pattern configured to cause a positive thrombogenic response when exposed to blood flow.

* * * * *